United States Patent
Levi et al.

(10) Patent No.: US 10,932,903 B2
(45) Date of Patent: Mar. 2, 2021

(54) SKIRT ASSEMBLY FOR IMPLANTABLE PROSTHETIC VALVE

(71) Applicant: Edwards Lifesciences Corporation, Irvine, CA (US)

(72) Inventors: Tamir S. Levi, Zikhron Yaakov (IL); Yair A. Neumann, Moshav Sede Varburg (IL)

(73) Assignee: Edwards Lifesciences Corporation, Irvine, CA (US)

( * ) Notice: Subject to any disclaimer, the term of this patent is extended or adjusted under 35 U.S.C. 154(b) by 5 days.

(21) Appl. No.: 16/059,913

(22) Filed: Aug. 9, 2018

(65) Prior Publication Data

US 2019/0053897 A1 Feb. 21, 2019

Related U.S. Application Data

(60) Provisional application No. 62/545,916, filed on Aug. 15, 2017.

(51) Int. Cl.
*A61F 2/24* (2006.01)

(52) U.S. Cl.
CPC .......... *A61F 2/2415* (2013.01); *A61F 2/2418* (2013.01); *A61F 2210/0076* (2013.01);
(Continued)

(58) Field of Classification Search
CPC .................................. A61F 2/24; A61F 2/2415
See application file for complete search history.

(56) References Cited

U.S. PATENT DOCUMENTS

| 3,409,013 A | 11/1968 | Berry |
| 3,548,417 A | 12/1970 | Kisher |

(Continued)

FOREIGN PATENT DOCUMENTS

| DE | 2246526 A1 | 3/1973 |
| DE | 19532846 A1 | 3/1997 |

(Continued)

OTHER PUBLICATIONS

H.R. Andersen, et al. "Transluminal Implantation of Artificial Heart Valve. Description of a New Expandable Aortic Valve and Initial Results with implantation by Catheter Technique in Closed Chest Pig," European Heart Journal, No. 13. pp. 704-708. 1992.

(Continued)

*Primary Examiner* — Matthew W Schall
(74) *Attorney, Agent, or Firm* — Edwards Lifesciences; Hans P. Smith

(57) ABSTRACT

Embodiments of an implantable prosthetic valve are disclosed. The valve can have an annular frame having a plurality of frame members and a skirt assembly. The skirt assembly can include a laminate having a fabric layer sandwiched between a first covering member and a second covering member. At least one surface of the fabric layer can be exposed at one or more windows in the second covering member. The skirt assembly can be coupled to the annular frame by a suture extending through the fabric layer at the one or more windows and around at least one of the plurality of frame members. Methods for making such an implantable prosthetic valve are also disclosed.

20 Claims, 5 Drawing Sheets

(52) U.S. Cl.
CPC .......... A61F 2220/0075 (2013.01); A61F 2230/0054 (2013.01); A61F 2250/0039 (2013.01); A61F 2250/0069 (2013.01)

(56) References Cited

U.S. PATENT DOCUMENTS

| | | | |
|---|---|---|---|
| 3,587,115 A | 6/1971 | Shiley |
| 3,657,744 A | 4/1972 | Ersek |
| 3,671,979 A | 6/1972 | Moulopoulos |
| 3,714,671 A | 2/1973 | Edwards et al. |
| 3,755,823 A | 9/1973 | Hancock |
| 4,035,849 A | 7/1977 | Angell et al. |
| 4,056,854 A | 11/1977 | Boretos et al. |
| 4,106,129 A | 8/1978 | Carpentier et al. |
| 4,222,126 A | 9/1980 | Boretos et al. |
| 4,265,694 A | 5/1981 | Boretos et al. |
| 4,297,749 A | 11/1981 | Davis et al. |
| RE30,912 E | 4/1982 | Hancock |
| 4,339,831 A | 7/1982 | Johnson |
| 4,343,048 A | 8/1982 | Ross et al. |
| 4,345,340 A | 8/1982 | Rosen |
| 4,373,216 A | 2/1983 | Klawitter |
| 4,406,022 A | 9/1983 | Roy |
| 4,441,216 A | 4/1984 | Ionescu et al. |
| 4,470,157 A | 9/1984 | Love |
| 4,535,483 A | 8/1985 | Klawitter et al. |
| 4,574,803 A | 3/1986 | Storz |
| 4,592,340 A | 6/1986 | Boyles |
| 4,605,407 A | 8/1986 | Black et al. |
| 4,612,011 A | 9/1986 | Kautzky |
| 4,643,732 A | 2/1987 | Pietsch et al. |
| 4,655,771 A | 4/1987 | Wallsten |
| 4,692,164 A | 9/1987 | Dzemeshkevich et al. |
| 4,733,665 A | 3/1988 | Palmaz |
| 4,759,758 A | 7/1988 | Gabbay |
| 4,762,128 A | 8/1988 | Rosenbluth |
| 4,777,951 A | 10/1988 | Cribier et al. |
| 4,787,899 A | 11/1988 | Lazarus |
| 4,787,901 A | 11/1988 | Baykut |
| 4,796,629 A | 1/1989 | Grayzel |
| 4,820,299 A | 4/1989 | Philippe et al. |
| 4,829,990 A | 5/1989 | Thuroff et al. |
| 4,851,001 A | 7/1989 | Taheri |
| 4,856,516 A | 8/1989 | Hillstead |
| 4,878,495 A | 11/1989 | Grayzel |
| 4,878,906 A | 11/1989 | Lindemann et al. |
| 4,883,458 A | 11/1989 | Shiber |
| 4,922,905 A | 5/1990 | Strecker |
| 4,966,604 A | 10/1990 | Reiss |
| 4,979,939 A | 12/1990 | Shiber |
| 4,986,830 A | 1/1991 | Owens et al. |
| 4,994,077 A | 2/1991 | Dobben |
| 5,007,896 A | 4/1991 | Shiber |
| 5,026,366 A | 6/1991 | Leckrone |
| 5,032,128 A | 7/1991 | Alonso |
| 5,037,434 A | 8/1991 | Lane |
| 5,047,041 A | 9/1991 | Samuels |
| 5,059,177 A | 10/1991 | Towne et al. |
| 5,080,668 A | 1/1992 | Bolz et al. |
| 5,085,635 A | 2/1992 | Cragg |
| 5,089,015 A | 2/1992 | Ross |
| 5,152,771 A | 10/1992 | Sabbaghian et al. |
| 5,163,953 A | 11/1992 | Vince |
| 5,167,628 A | 12/1992 | Boyles |
| 5,192,297 A | 3/1993 | Hull |
| 5,266,073 A | 11/1993 | Wall |
| 5,282,847 A | 2/1994 | Trescony et al. |
| 5,295,958 A | 3/1994 | Shturman |
| 5,332,402 A | 7/1994 | Teitelbaum |
| 5,360,444 A | 11/1994 | Kusuhara |
| 5,370,685 A | 12/1994 | Stevens |
| 5,397,351 A | 3/1995 | Pavcnik et al. |
| 5,411,055 A | 5/1995 | Kane |
| 5,411,552 A | 5/1995 | Andersen et al. |
| 5,443,446 A | 8/1995 | Shturman |
| 5,480,424 A | 1/1996 | Cox |
| 5,500,014 A | 3/1996 | Quijano et al. |
| 5,545,209 A | 8/1996 | Roberts et al. |
| 5,545,214 A | 8/1996 | Stevens |
| 5,549,665 A | 8/1996 | Vesely et al. |
| 5,554,185 A | 9/1996 | Block et al. |
| 5,558,644 A | 9/1996 | Boyd et al. |
| 5,571,175 A | 11/1996 | Vanney et al. |
| 5,584,803 A | 12/1996 | Stevens et al. |
| 5,591,185 A | 1/1997 | Kilmer et al. |
| 5,591,195 A | 1/1997 | Taheri et al. |
| 5,607,464 A | 3/1997 | Trescony et al. |
| 5,609,626 A | 3/1997 | Quijano et al. |
| 5,628,792 A | 5/1997 | Lentell |
| 5,639,274 A | 6/1997 | Fischell et al. |
| 5,665,115 A | 9/1997 | Cragg |
| 5,716,417 A | 2/1998 | Girard et al. |
| 5,728,068 A | 3/1998 | Leone et al. |
| 5,749,890 A | 5/1998 | Shaknovich |
| 5,756,476 A | 5/1998 | Epstein et al. |
| 5,769,812 A | 6/1998 | Stevens et al. |
| 5,800,508 A | 9/1998 | Goicoechea et al. |
| 5,840,081 A | 11/1998 | Andersen et al. |
| 5,855,597 A | 1/1999 | Jayaraman |
| 5,855,601 A | 1/1999 | Bessler et al. |
| 5,855,602 A | 1/1999 | Angell |
| 5,925,063 A | 7/1999 | Khosravi |
| 5,957,949 A | 9/1999 | Leonhardt et al. |
| 6,027,525 A | 2/2000 | Suh et al. |
| 6,132,473 A | 10/2000 | Williams et al. |
| 6,168,614 B1 | 1/2001 | Andersen et al. |
| 6,171,335 B1 | 1/2001 | Wheatley et al. |
| 6,174,327 B1 | 1/2001 | Mertens et al. |
| 6,210,408 B1 | 4/2001 | Chandrasekaran et al. |
| 6,217,585 B1 | 4/2001 | Houser et al. |
| 6,221,091 B1 | 4/2001 | Khosravi |
| 6,231,602 B1 | 5/2001 | Carpentier et al. |
| 6,245,102 B1 | 6/2001 | Jayaraman |
| 6,299,637 B1 | 10/2001 | Shaolian et al. |
| 6,302,906 B1 | 10/2001 | Goicoechea et al. |
| 6,338,740 B1 | 1/2002 | Carpentier |
| 6,350,277 B1 | 2/2002 | Kocur |
| 6,352,547 B1 | 3/2002 | Brown et al. |
| 6,425,916 B1 | 7/2002 | Garrison et al. |
| 6,440,764 B1 | 8/2002 | Focht et al. |
| 6,454,799 B1 | 9/2002 | Schreck |
| 6,458,153 B1 | 10/2002 | Bailey et al. |
| 6,461,382 B1 | 10/2002 | Cao |
| 6,468,660 B2 | 10/2002 | Ogle et al. |
| 6,482,228 B1 | 11/2002 | Norred |
| 6,488,704 B1 | 12/2002 | Connelly et al. |
| 6,527,979 B2 | 3/2003 | Constantz et al. |
| 6,569,196 B1 | 5/2003 | Vesely |
| 6,582,462 B1 | 6/2003 | Andersen et al. |
| 6,605,112 B1 | 8/2003 | Moll et al. |
| 6,652,578 B2 | 11/2003 | Bailey et al. |
| 6,689,123 B2 | 2/2004 | Pinchasik |
| 6,716,244 B2 | 4/2004 | Klaco |
| 6,730,118 B2 | 5/2004 | Spenser et al. |
| 6,733,525 B2 | 5/2004 | Yang et al. |
| 6,767,362 B2 | 7/2004 | Schreck |
| 6,769,161 B2 | 8/2004 | Brown et al. |
| 6,783,542 B2 | 8/2004 | Eidenschink |
| 6,830,584 B1 | 12/2004 | Seguin |
| 6,878,162 B2 | 4/2005 | Bales et al. |
| 6,893,460 B2 | 5/2005 | Spenser et al. |
| 6,908,481 B2 | 6/2005 | Cribier |
| 6,936,067 B2 | 8/2005 | Buchanan |
| 7,018,406 B2 | 3/2006 | Seguin et al. |
| 7,018,408 B2 | 3/2006 | Bailey et al. |
| 7,096,554 B2 | 8/2006 | Austin et al. |
| 7,225,518 B2 | 6/2007 | Eidenschink et al. |
| 7,276,078 B2 | 10/2007 | Spenser et al. |
| 7,276,084 B2 | 10/2007 | Yang et al. |
| 7,316,710 B1 | 1/2008 | Cheng et al. |
| 7,318,278 B2 | 1/2008 | Zhang et al. |
| 7,374,571 B2 | 5/2008 | Pease et al. |
| 7,393,360 B2 | 7/2008 | Spenser et al. |
| 7,462,191 B2 | 12/2008 | Spenser et al. |

(56) References Cited

U.S. PATENT DOCUMENTS

| | | |
|---|---|---|
| 7,510,575 B2 | 3/2009 | Spenser et al. |
| 7,563,280 B2 | 7/2009 | Anderson et al. |
| 7,585,321 B2 | 9/2009 | Cribier |
| 7,618,446 B2 | 11/2009 | Andersen et al. |
| 7,618,447 B2 | 11/2009 | Case et al. |
| 7,655,034 B2 | 2/2010 | Mitchell et al. |
| 7,785,366 B2 | 8/2010 | Maurer et al. |
| 7,959,665 B2 | 6/2011 | Pienknagura |
| 7,959,672 B2 | 6/2011 | Salahieh et al. |
| 7,993,394 B2 | 8/2011 | Hariton et al. |
| 8,029,556 B2 | 10/2011 | Rowe |
| 8,075,611 B2 | 12/2011 | Millwee et al. |
| 8,128,686 B2 | 3/2012 | Paul, Jr. et al. |
| 8,167,932 B2 | 5/2012 | Bourang et al. |
| 8,291,570 B2 | 10/2012 | Eidenschink et al. |
| 8,348,998 B2 | 1/2013 | Pintor et al. |
| 8,449,606 B2 | 5/2013 | Eliasen et al. |
| 8,454,685 B2 | 6/2013 | Hariton et al. |
| 8,652,203 B2 | 2/2014 | Quadri et al. |
| 8,747,463 B2 | 6/2014 | Fogarty et al. |
| 9,078,781 B2 | 7/2015 | Ryan et al. |
| 2001/0021872 A1 | 9/2001 | Bailey et al. |
| 2002/0026094 A1 | 2/2002 | Roth |
| 2002/0032481 A1 | 3/2002 | Gabbay |
| 2002/0138135 A1 | 9/2002 | Duerig et al. |
| 2002/0143390 A1 | 10/2002 | Ishii |
| 2002/0173842 A1 | 11/2002 | Buchanan |
| 2003/0014105 A1 | 1/2003 | Cao |
| 2003/0050694 A1 | 3/2003 | Yang et al. |
| 2003/0100939 A1 | 5/2003 | Yodfat et al. |
| 2003/0158597 A1 | 8/2003 | Quiachon et al. |
| 2003/0212454 A1 | 11/2003 | Scott et al. |
| 2004/0024452 A1 | 2/2004 | Kruse et al. |
| 2004/0039436 A1 | 2/2004 | Spenser et al. |
| 2004/0078074 A1 | 4/2004 | Anderson et al. |
| 2004/0186558 A1 | 9/2004 | Pavcnik et al. |
| 2004/0186563 A1 | 9/2004 | Lobbi |
| 2004/0186565 A1 | 9/2004 | Schreck |
| 2004/0260389 A1 | 12/2004 | Case et al. |
| 2005/0010285 A1 | 1/2005 | Lambrecht et al. |
| 2005/0075725 A1 | 4/2005 | Rowe |
| 2005/0075728 A1 | 4/2005 | Nguyen et al. |
| 2005/0096736 A1 | 5/2005 | Osse et al. |
| 2005/0096738 A1 | 5/2005 | Cali et al. |
| 2005/0188525 A1 | 9/2005 | Weber et al. |
| 2005/0203614 A1 | 9/2005 | Forster et al. |
| 2005/0203617 A1 | 9/2005 | Forster et al. |
| 2005/0234546 A1 | 10/2005 | Nugent et al. |
| 2006/0004469 A1 | 1/2006 | Sokel |
| 2006/0025857 A1 | 2/2006 | Bergheim et al. |
| 2006/0058872 A1 | 3/2006 | Salahieh et al. |
| 2006/0074484 A1 | 4/2006 | Huber |
| 2006/0108090 A1 | 5/2006 | Ederer et al. |
| 2006/0149350 A1 | 7/2006 | Patel et al. |
| 2006/0183383 A1 | 8/2006 | Asmus et al. |
| 2006/0229719 A1 | 10/2006 | Marquez et al. |
| 2006/0259136 A1 | 11/2006 | Nguyen et al. |
| 2006/0259137 A1 | 11/2006 | Artof et al. |
| 2006/0287717 A1 | 12/2006 | Rowe et al. |
| 2007/0005131 A1 | 1/2007 | Taylor |
| 2007/0010876 A1 | 1/2007 | Salahieh et al. |
| 2007/0010877 A1 | 1/2007 | Salahieh et al. |
| 2007/0027535 A1* | 2/2007 | Purdy, Jr. ............... A61F 2/2412 623/2.18 |
| 2007/0112422 A1 | 5/2007 | Dehdashtian |
| 2007/0162102 A1 | 7/2007 | Ryan et al. |
| 2007/0203503 A1 | 8/2007 | Salahieh et al. |
| 2007/0203575 A1 | 8/2007 | Forster et al. |
| 2007/0203576 A1 | 8/2007 | Lee et al. |
| 2007/0208550 A1 | 9/2007 | Cao et al. |
| 2007/0213813 A1 | 9/2007 | Von Segesser et al. |
| 2007/0233228 A1 | 10/2007 | Eberhardt et al. |
| 2007/0260305 A1 | 11/2007 | Drews et al. |
| 2007/0265700 A1 | 11/2007 | Eliasen et al. |
| 2008/0021546 A1 | 1/2008 | Patz et al. |
| 2008/0114442 A1 | 5/2008 | Mitchell et al. |
| 2008/0125853 A1 | 5/2008 | Bailey et al. |
| 2008/0154355 A1 | 6/2008 | Benichou et al. |
| 2008/0183271 A1 | 7/2008 | Frawley et al. |
| 2008/0208327 A1 | 8/2008 | Rowe |
| 2008/0243245 A1 | 10/2008 | Thambar et al. |
| 2008/0255660 A1 | 10/2008 | Guyenot et al. |
| 2008/0275537 A1 | 11/2008 | Limon |
| 2008/0294248 A1 | 11/2008 | Yang et al. |
| 2009/0118826 A1 | 5/2009 | Khaghani |
| 2009/0125118 A1 | 5/2009 | Gong |
| 2009/0157175 A1 | 6/2009 | Benichou |
| 2009/0276040 A1 | 11/2009 | Rowe et al. |
| 2009/0281619 A1 | 11/2009 | Le et al. |
| 2009/0287296 A1 | 11/2009 | Manasse |
| 2009/0287299 A1 | 11/2009 | Tabor et al. |
| 2009/0299452 A1 | 12/2009 | Eidenschink et al. |
| 2009/0319037 A1 | 12/2009 | Rowe et al. |
| 2010/0023120 A1 | 1/2010 | Holecek et al. |
| 2010/0049313 A1 | 2/2010 | Alon et al. |
| 2010/0082094 A1 | 4/2010 | Quadri et al. |
| 2010/0168844 A1 | 7/2010 | Toomes et al. |
| 2010/0185277 A1 | 7/2010 | Braido et al. |
| 2010/0198347 A1 | 8/2010 | Zakay et al. |
| 2010/0204781 A1 | 8/2010 | Alkhatib |
| 2011/0015729 A1 | 1/2011 | Jimenez et al. |
| 2011/0022157 A1 | 1/2011 | Essinger et al. |
| 2011/0066224 A1 | 3/2011 | White |
| 2011/0137397 A1 | 6/2011 | Chau et al. |
| 2011/0218619 A1 | 9/2011 | Benichou et al. |
| 2011/0295363 A1 | 12/2011 | Girard et al. |
| 2011/0319991 A1 | 12/2011 | Hariton et al. |
| 2012/0089223 A1 | 4/2012 | Nguyen et al. |
| 2012/0101571 A1 | 4/2012 | Thambar et al. |
| 2012/0123529 A1 | 5/2012 | Levi et al. |
| 2012/0259409 A1 | 10/2012 | Nguyen et al. |
| 2013/0023985 A1 | 1/2013 | Khairkhahan et al. |
| 2013/0046373 A1 | 2/2013 | Cartledge et al. |
| 2013/0150956 A1 | 6/2013 | Yohanan et al. |
| 2013/0166017 A1 | 6/2013 | Cartledge et al. |
| 2013/0190857 A1 | 7/2013 | Mitra et al. |
| 2013/0274873 A1 | 10/2013 | Delaloye et al. |
| 2013/0310926 A1 | 11/2013 | Hariton |
| 2013/0317598 A1 | 11/2013 | Rowe et al. |
| 2013/0331929 A1 | 12/2013 | Mitra et al. |
| 2014/0194981 A1 | 7/2014 | Menk et al. |
| 2014/0200661 A1 | 7/2014 | Pintor et al. |
| 2014/0209238 A1 | 7/2014 | Bonyuet et al. |
| 2014/0222136 A1 | 8/2014 | Geist et al. |
| 2014/0277417 A1 | 9/2014 | Schraut et al. |
| 2014/0277419 A1 | 9/2014 | Garde et al. |
| 2014/0277424 A1 | 9/2014 | Oslund |
| 2014/0277563 A1 | 9/2014 | White |
| 2014/0296962 A1 | 10/2014 | Cartledge et al. |
| 2014/0330372 A1 | 11/2014 | Weston et al. |
| 2014/0343670 A1 | 11/2014 | Bakis et al. |
| 2014/0343671 A1 | 11/2014 | Yohanan et al. |
| 2014/0350667 A1 | 11/2014 | Braido et al. |
| 2015/0073545 A1 | 3/2015 | Braido |
| 2015/0073546 A1 | 3/2015 | Braido |
| 2015/0135506 A1 | 5/2015 | White |
| 2015/0157455 A1 | 6/2015 | Hoang et al. |
| 2017/0014229 A1 | 1/2017 | Nguyen-Thien-Nhon et al. |
| 2018/0028310 A1 | 2/2018 | Gurovich et al. |
| 2018/0153689 A1 | 6/2018 | Maimon et al. |
| 2018/0325665 A1 | 11/2018 | Gurovich et al. |
| 2018/0344456 A1 | 12/2018 | Barash et al. |

FOREIGN PATENT DOCUMENTS

| | | |
|---|---|---|
| DE | 19546692 A1 | 6/1997 |
| DE | 19857887 A1 | 7/2000 |
| DE | 19907646 A1 | 8/2000 |
| DE | 10049812 A1 | 4/2002 |
| DE | 10049813 C1 | 4/2002 |
| DE | 10049814 A1 | 4/2002 |
| DE | 10049815 A1 | 4/2002 |
| EP | 0103546 A1 | 3/1984 |
| EP | 0850607 A1 | 7/1998 |

(56) References Cited

FOREIGN PATENT DOCUMENTS

| | | | |
|---|---|---|---|
| EP | 1057460 A1 | 12/2000 |
| EP | 1088529 A2 | 4/2001 |
| EP | 1570809 A1 | 9/2005 |
| FR | 2788217 A1 | 7/2000 |
| FR | 2815844 A1 | 5/2002 |
| GB | 2056023 A | 3/1981 |
| SU | 1271508 A1 | 11/1986 |
| WO | 9117720 A1 | 11/1991 |
| WO | 9217118 A1 | 10/1992 |
| WO | 9301768 A1 | 2/1993 |
| WO | 9724080 A1 | 7/1997 |
| WO | 9829057 A1 | 7/1998 |
| WO | 9930646 A1 | 6/1999 |
| WO | 9933414 A1 | 7/1999 |
| WO | 0018333 A1 | 4/2000 |
| WO | 0041652 A1 | 7/2000 |
| WO | 0047139 A1 | 8/2000 |
| WO | 0135878 A2 | 5/2001 |
| WO | 0149213 A2 | 7/2001 |
| WO | 0154624 A1 | 8/2001 |
| WO | 0154625 A1 | 8/2001 |
| WO | 0162189 A1 | 8/2001 |
| WO | 0164137 A1 | 9/2001 |
| WO | 0176510 A2 | 10/2001 |
| WO | 0222054 A1 | 3/2002 |
| WO | 0236048 A1 | 5/2002 |
| WO | 0241789 A2 | 5/2002 |
| WO | 0243620 A1 | 6/2002 |
| WO | 0247575 A2 | 6/2002 |
| WO | 0249540 A2 | 6/2002 |
| WO | 03047468 A1 | 6/2003 |
| WO | 2005034812 A1 | 4/2005 |
| WO | 2005055883 A1 | 6/2005 |
| WO | 2005084595 A1 | 9/2005 |
| WO | 2005102015 A2 | 11/2005 |
| WO | 2006014233 A2 | 2/2006 |
| WO | 2006032051 A2 | 3/2006 |
| WO | 2006034008 A2 | 3/2006 |
| WO | 2006111391 A1 | 10/2006 |
| WO | 2006127089 A1 | 11/2006 |
| WO | 2006138173 A2 | 12/2006 |
| WO | 2007047488 A2 | 4/2007 |
| WO | 2007067942 A1 | 6/2007 |
| WO | 2007097983 A2 | 8/2007 |
| WO | 2008005405 A2 | 1/2008 |
| WO | 2008015257 A2 | 2/2008 |
| WO | 2008035337 A2 | 3/2008 |
| WO | 2008091515 A2 | 7/2008 |
| WO | 2008147964 A1 | 12/2008 |
| WO | 2008150529 A1 | 12/2008 |
| WO | 2009033469 A1 | 3/2009 |
| WO | 2009042196 A2 | 4/2009 |
| WO | 2009053497 A1 | 4/2009 |
| WO | 2009061389 A2 | 5/2009 |
| WO | 2009116041 | 9/2009 |
| WO | 2009149462 A2 | 12/2009 |
| WO | 2010011699 A2 | 1/2010 |
| WO | 2010121076 A2 | 10/2010 |
| WO | 2013106585 A1 | 7/2013 |
| WO | 2015085218 A1 | 6/2015 |

OTHER PUBLICATIONS

H.R. Andersen "History of Percutaneous Aortic Valve Prosthesis," Herz No. 34. pp. 343-346. 2009.

Pavcnik, et al. "Development and initial Experimental Evaluation of a Prosthetic Aortic Valve for Transcatheter Placement," Cardiovascular Radiology, vol. 183, No. 1. pp. 151-154. 1992.

Bailey, S. "Percutaneous Expandable Prosthetic Valves," Textbook of Interventional Cardiology vol. 2, 2nd Ed. pp. 1268-1276. 1994.

Al-Khaja, et al. "Eleven Years' Experience with Carpentier-Edwards Biological Valves in Relation to Survival and Complications," European Journal of Cardiothoracic Surgery, vol. 3. pp. 305-311. 1989.

Ross, "Aortic Valve Surgery," At a meeting of the Council on Aug. 4, 1966. pp. 192-197.

Sabbah, et al. "Mechanical Factors in the Degeneration of Porcine Bioprosthetic Valves: An Overview," Journal of Cardiac Surgery, vol. 4, No. 4. pp. 302-309. 1989.

Wheatley, "Valve Prostheses," Operative Surgery, 4th ed. pp. 415-424. 1986.

Uchida, "Modifications of Gianturco Expandable Wire Stents," American Journal of Roentgenology, vol. 150. pp. 1185-1187. 1986.

\* cited by examiner

SKIRT ASSEMBLY FOR IMPLANTABLE PROSTHETIC VALVE

CROSS-REFERENCE TO RELATED APPLICATION

The present application claims the benefit of U.S. Provisional Application No. 62/545,916, filed Aug. 15, 2017, which is incorporated herein by reference.

FIELD

The present disclosure concerns embodiments of a prosthetic valve for implantation into body ducts, such as native heart valve annuluses.

BACKGROUND

The human heart can suffer from various valvular diseases. These valvular diseases can result in significant malfunctioning of the heart and ultimately require replacement of the native valve with an artificial valve. There are a number of known artificial valves and a number of known methods of implanting these artificial valves in humans.

Various surgical techniques may be used to replace or repair a diseased or damaged valve. Due to stenosis and other heart valve diseases, thousands of patients undergo surgery each year wherein the defective native heart valve is replaced by a prosthetic valve. Another less drastic method for treating defective valves is through repair or reconstruction, which is typically used on minimally calcified valves. The problem with surgical therapy is the significant risk it imposes on these chronically ill patients with high morbidity and mortality rates associated with surgical repair.

When the native valve is replaced, surgical implantation of the prosthetic valve typically requires an open-chest surgery during which the heart is stopped and patient placed on cardiopulmonary bypass (a so-called "heart-lung machine"). In one common surgical procedure, the diseased native valve leaflets are excised and a prosthetic valve is sutured to the surrounding tissue at the valve annulus. Because of the trauma associated with the procedure and the attendant duration of extracorporeal blood circulation, some patients do not survive the surgical procedure or die shortly thereafter. It is well known that the risk to the patient increases with the amount of time required on extracorporeal circulation. Due to these risks, a substantial number of patients with defective native valves are deemed inoperable because their condition is too frail to withstand the procedure. By some estimates, more than 50% of the subjects suffering from valve stenosis who are older than 80 years cannot be operated on for valve replacement.

Because of the drawbacks associated with conventional open-heart surgery, percutaneous and minimally-invasive surgical approaches are garnering intense attention. In one technique, a prosthetic valve is configured to be implanted in a much less invasive procedure by way of catheterization. For instance, U.S. Pat. Nos. 5,411,522 and 6,730,118, which are incorporated herein by reference, describe collapsible transcatheter heart valves that can be percutaneously introduced in a compressed state on a catheter and expanded in the desired position by balloon inflation or by utilization of a self-expanding frame or stent.

Known prosthetic valves include a frame with a valvular structure (e.g., leaflets) mounted therein, an inner skirt secured to the inside of the frame, and optionally, an outer skirt secured to the exterior of the frame. The inner skirt can serve several functions. For example, the inner skirt can function as a seal member to prevent (or decrease) perivalvular leakage, to anchor the leaflets to the frame, and to protect the leaflets against damage caused by contact with the frame during crimping and during working cycles of the valve. The outer skirt can cooperate with the inner skirt to further reduce or avoid perivalvular leakage after implantation of the valve. The inner skirt desirably includes a tough, tear resistant material such as polyethylene terephthalate (PET), although various other synthetic or natural materials can be used.

The inner and outer skirts are frequently secured to the frame by suturing or stitching the fabric of the respective skirts to the frame. Suturing of the inner skirt to the frame can expose the leaflets to the sutures. During working cycles of the valve, repetitive contact between the leaflets and the exposed sutures as well as contact between the leaflets and the fabric material of the skirt can cause abrasion of the leaflets. Accordingly, improvements to skirts for prosthetic valves are desirable.

SUMMARY

The present disclosure is directed toward methods and apparatuses relating to prosthetic valves, such as prosthetic heart valves.

Certain embodiments of the disclosure concern methods for making an implantable prosthetic valve. One exemplary embodiment of the method includes forming a laminate comprising a fabric layer disposed between first and second covering members. The second covering member can include one or more windows where the fabric layer is exposed. The method further includes placing the laminate against an annular frame, and suturing the laminate to the annular frame by threading a suture through the fabric layer at the one or more windows of the second covering member and around a portion of the frame.

In certain embodiments, the laminate can comprise an annular skirt sized and shaped to cover openings in the frame to prevent blood from flowing through the frame openings.

In certain embodiments, the skirt can be positioned inside of the annular frame.

In the foregoing embodiments, the first and second covering members can be fused to each other through openings in the fabric layer.

In the foregoing embodiments, forming the laminate can include forming the first covering member by electrospinning, placing the fabric layer on the electrospun first covering member, and forming the second covering member on the fabric layer by electrospinning.

In certain embodiments, forming the laminate can further include masking one or more areas on the fabric layer prior to forming the second covering member so as to form the one or more windows in the second covering member when the second covering member is formed over the fabric layer.

In certain embodiments, forming the laminate can include masking one or more areas on at least one side of the fabric layer with a masking material, dipping the fabric layer in a liquefied polymeric material, allowing the liquefied polymeric material to cure, and removing the masking material to form the one or more windows in the laminate.

In certain embodiments, the one or more windows in the second covering member can extend continuously around the laminate in a circumferential direction.

In certain embodiments, the first and second covering members comprise elastomeric material.

In certain embodiments, the elastomeric material can include expanded polytetrafluoroethylene (ePTFE) or ultra-high molecular weight polyethylene (UHMWPE) or polyurethane.

Certain embodiments of the disclosure concern also concern implantable prosthetic valves. One representative implantable prosthetic valve can include an annular frame having a plurality of frame members and a skirt assembly. The skirt assembly can include a laminate having a fabric layer sandwiched between a first covering member and a second covering member. The fabric layer can be exposed at one or more windows in the second covering member. The skirt assembly can be coupled to the annular frame by a suture extending through the fabric layer at the one or more windows and around at least one of the plurality of frame members.

In certain embodiments, the skirt assembly can be positioned inside of the annular frame.

In certain embodiments, the implantable prosthetic valve can further include a plurality of leaflets sutured to the skirt assembly. The leaflets can be configured to permit blood flow in a first direction through the prosthetic valve and block blood flow through the prosthetic valve in a second direction, opposite the first direction.

In the foregoing embodiments of the implantable prosthetic valve, the first and second covering members can be fused to each other through openings in the fabric layer.

In the foregoing embodiments of the implantable prosthetic valve, the first covering member or the second covering member can include a membrane of non-woven fibers.

In the foregoing embodiments of the implantable prosthetic valve, the first or second covering member can be non-absorbable and have a porous microstructure that promotes ingrowth of surrounding tissue to assist in securing the prosthetic valve in a body lumen.

In the foregoing embodiments of the implantable prosthetic valve, the annular frame can have an inlet end and an outlet end, and be configured to be radially collapsible and expandable. The plurality of frame members can define a plurality of gaps between the frame members, and the skirt assembly can be configured to prevent blood from flowing through those gaps in the frame that are covered by the skirt assembly.

In certain embodiments, the skirt assembly can be sutured to the frame only at the one or more windows in the second covering member.

In certain embodiments, the first covering member and the second covering member can comprise elastomeric material.

In certain embodiments, the elastomeric material can include ePTFE or UHMWPE or polyurethane.

The foregoing and other objects, features, and advantages of the invention will become more apparent from the following detailed description, which proceeds with reference to the accompanying figures.

DETAILED DESCRIPTION

Figure 1:
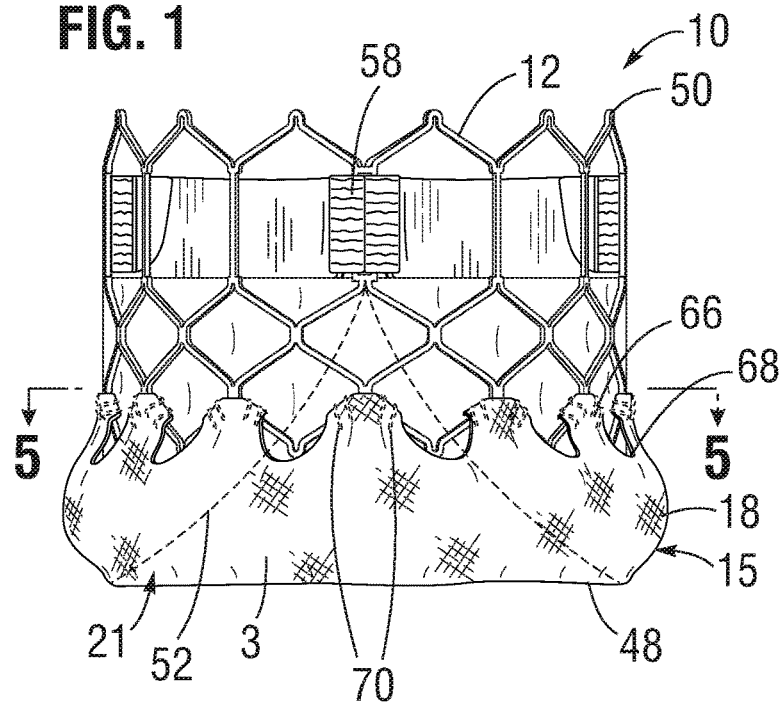
FIG. 1 shows a side elevation view of an exemplary embodiment of an implantable prosthetic valve.
Figure 2:
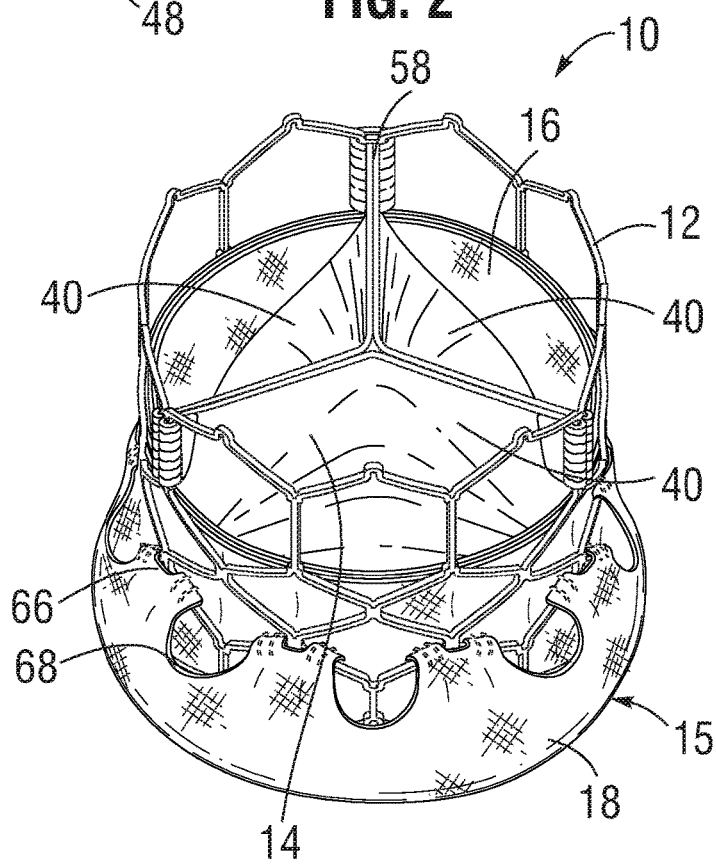
FIG. 2 shows a top perspective view of the prosthetic valve of FIG. 1.

FIGS. 1-2 show two different views of a prosthetic valve 10, according to one embodiment. The illustrated valve is adapted to be implanted in the native aortic annulus, although in other embodiments it can be adapted to be implanted in the other native annuluses of the heart. The valve 10 can have several main components: a stent, or frame, 12, a valvular structure 14, and a skirt assembly 15. The skirt assembly 15 can include an inner skirt 16, and optionally, an outer skirt 18.

The valvular structure 14 (or leaflet structure) can include three leaflets 40 (although a greater or fewer number of leaflets can be used), collectively forming the leaflet structure, which can be arranged to collapse in a tricuspid arrangement. The valvular structure 14 is configured to permit blood to flow through the prosthetic valve 10 in a direction from an inlet end 48 of the prosthetic valve to an outlet end 50 of the prosthetic valve and to block the flow of blood through the prosthetic valve in a direction from the outlet end 50 to the inlet end 48.

Each leaflet 40 desirably has a curved, generally U-shaped inlet or cusp edge 52. In this manner, the inlet edge of the valvular structure 14 has an undulating, curved scalloped shape. By forming the leaflets with this scalloped geometry, stresses on the leaflets can be reduced, which in turn improves durability of the valve. Moreover, by virtue of the scalloped shape, folds and ripples at the belly of each leaflet (the central region of each leaflet), which can cause early calcification in those areas, can be eliminated or at least minimized. The scalloped geometry also reduces the amount of tissue material used to form leaflet structure, thereby allowing a smaller, more even crimped profile at the inflow end of the valve. The leaflets 40 can be formed of pericardial tissue (e.g., bovine pericardial tissue), biocompatible synthetic materials, or various other suitable natural or synthetic materials as known in the art and described in U.S. Pat. No. 6,730,118, which is incorporated by reference herein.

Figure 3:
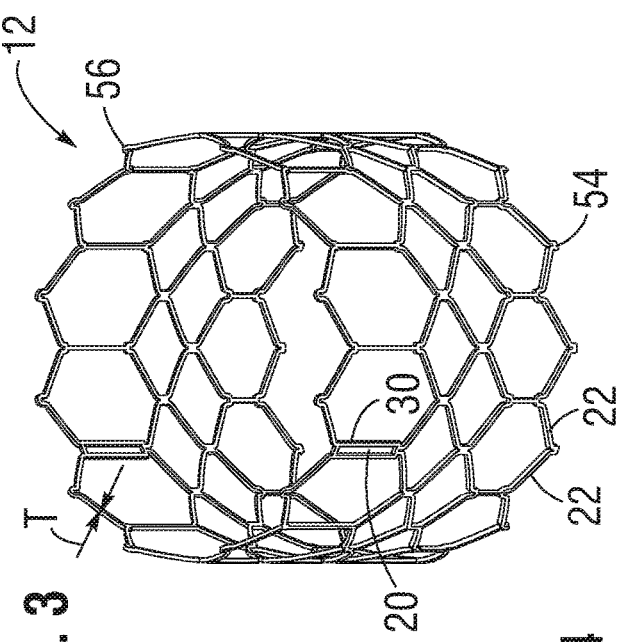
FIG. 3 shows an exemplary frame of the prosthetic valve of FIG. 1.

The bare frame 12 is shown in FIG. 3. In the depicted embodiment, the frame 12 has an annular shape defining an inlet end 54 and an outlet end 56 and includes a plurality of struts (or frame members). The frame 12 can be formed with a plurality of circumferentially spaced slots, or commissure windows, 20 (three in the illustrated embodiment) that are adapted to mount the commissures 58 of the valvular structure 14 to the frame, as described more fully in U.S. Patent Publication No. 2012/0123529, which is incorporated herein by reference.

The frame 12 can be made of any of various suitable plastically-expandable materials (e.g., stainless steel, etc.) or self-expanding materials (e.g., Nitinol) as known in the art. When constructed of a plastically-expandable material, the frame 12 (and thus the valve 10) can be crimped to a radially compressed state on a delivery catheter and then expanded inside a patient by an inflatable balloon or another suitable expansion mechanism. When constructed of a self-expandable material, the frame 12 (and thus the valve 10) can be crimped to a radially compressed state and restrained in the compressed state by insertion into a sheath or equivalent mechanism of a delivery catheter. Once inside the body, the valve can be advanced from the delivery sheath, which allows the valve to expand to its functional size.

Suitable plastically-expandable materials that can be used to form the frame 12 include, without limitation, stainless steel, a nickel based alloy (e.g., a cobalt-chromium or a nickel-cobalt-chromium alloy), polymers, or combinations thereof. In particular embodiments, frame 12 is made of a nickel-cobalt-chromium-molybdenum alloy, such as MP35N™ (tradename of SPS Technologies), which is equivalent to UNS R30035 (covered by ASTM F562-02). MP35N™/UNS R30035 comprises 35% nickel, 35% cobalt, 20% chromium, and 10% molybdenum, by weight. It has been found that the use of MP35N to form frame 12 provides superior structural results over stainless steel. In particular, when MP35N is used as the frame material, less material is needed to achieve the same or better performance in radial and crush force resistance, fatigue resistances, and corrosion resistance. Moreover, since less material is required, the crimped profile of the frame can be reduced, thereby providing a lower profile valve assembly for percutaneous delivery to the treatment location in the body.

Figure 4:
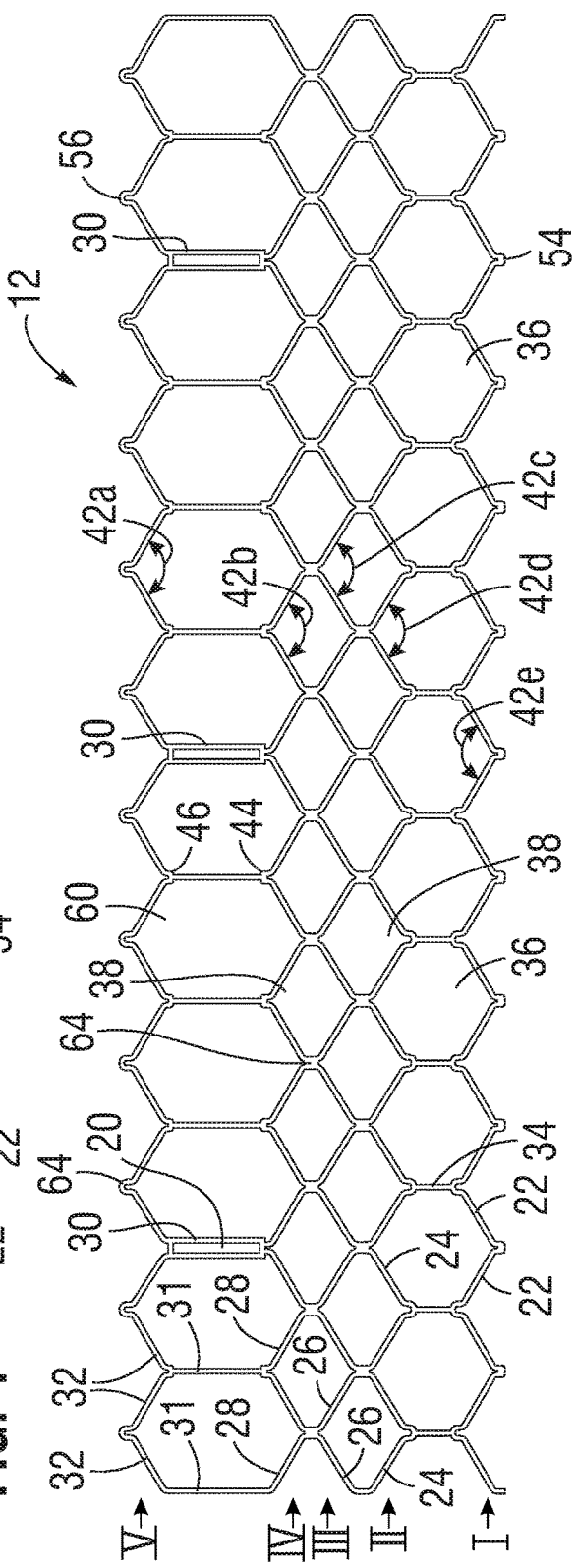
FIG. 4 shows is a flattened view of the frame shown in FIG. 3.

Referring to FIGS. 3 and 4, the frame 12 in the illustrated embodiment includes a first, lower row I of angled struts 22 arranged end-to-end and extending circumferentially at the inflow end of the frame; a second row II of circumferentially extending, angled struts 24; a third row III of circumferentially extending, angled struts 26; a fourth row IV of circumferentially extending, angled struts 28; and a fifth row V of circumferentially extending, angled struts 32 at the outflow end 56 of the frame. A plurality of substantially straight axially extending struts 34 can be used to interconnect the struts 22 of the first row I with the struts 24 of the second row II. The fifth row V of angled struts 32 are connected to the fourth row IV of angled struts 28 by a plurality of axially extending window frame portions 30 (which define the commissure windows 20) and a plurality of axially extending struts 31. Each axial strut 31 and each frame portion 30 extends from a location defined by the convergence of the lower ends of two angled struts 32 to another location defined by the convergence of the upper ends of two angled struts 28.

Each commissure window frame portion 30 mounts a respective commissure 58 of the leaflet structure 14. As can be seen, each frame portion 30 is secured at its upper and lower ends to the adjacent rows of struts to provide a robust configuration that enhances fatigue resistance under cyclic loading of the valve compared to known cantilevered struts for supporting the commissures of the leaflet structure. This configuration enables a reduction in the frame wall thickness to achieve a smaller crimped diameter of the valve. In particular embodiments, the thickness T of the frame 12 (FIG. 3) measured between the inner diameter and outer diameter is about 0.48 mm or less.

The struts and frame portions of the frame collectively define a plurality of open cells of the frame. At the inflow end of the frame 12, struts 22, struts 24, and struts 34 define a lower row of cells defining openings 36. The second, third, and fourth rows of struts 24, 26, and 28 define two intermediate rows of cells defining openings 38. The fourth and fifth rows of struts 28 and 32, along with frame portions 30 and struts 31, define an upper row of cells defining openings 60. The openings 60 are relatively large and are sized to allow portions of the leaflet structure 14 to protrude, or bulge, into and/or through the openings 60 when the frame 12 is crimped in order to minimize the crimping profile.

As shown in FIG. 4, the lower end of the strut 31 is connected to two struts 28 at a node or junction 44, and the upper end of the strut 31 is connected to two struts 32 at a node or junction 46. The strut 31 can have a thickness that is less than the thicknesses of the junctions 44, 46. The junctions 44, 46, along with junctions 64, each of which links two adjacent struts 32, prevent full closure of openings 60 when the frame 12 is in a crimped state. Thus, the geometry of the struts 31, and junctions 44, 46 and 64 assists in creating enough space in openings 60 in the crimped state to allow portions of the leaflets to protrude (i.e., bulge) outwardly through openings. This allows the valve to be crimped to a relatively smaller diameter than if all of the leaflet material is constrained within the crimped frame.

The frame 12 is configured to prevent or at least minimize possible over-expansion of the valve at a predetermined balloon pressure, especially at the outflow end portion of the frame, which supports the leaflet structure 14. In one aspect, the frame is configured to have relatively larger angles 42a, 42b, 42c, 42d, 42e between struts. The larger the angle, the greater the force required to open (expand) the frame. As such, the angles between the struts of the frame can be selected to limit radial expansion of the frame at a given opening pressure (e.g., inflation pressure of the balloon). In particular embodiments, these angles are at least 110 degrees or greater when the frame is expanded to its functional size, and even more particularly these angles are at least 120 degrees or greater when the frame is expanded to its functional size. U.S. Patent Publication No. 2012/0123529 further describes the frame 12 as well as other configurations for frames that can be incorporated in a prosthetic heart valve.

As shown in FIGS. 1-2, the skirt assembly 15 can include an inner skirt 16 that is located inside the frame 12 and an outer skirt 18 that is located outside the frame 12. The outer skirt 18 can include a plurality of circumferentially spaced apart extension portions or projections 66 and recesses 68 between adjacent projections formed along the outflow edge (the upper edge in the illustrated embodiment) of the outer skirt. In other embodiments, the outer skirt 18 can have a straight outflow edge without any projections or recesses.

The inflow (lower) and the outflow (upper) edges of the outer skirt 18 can be secured to the frame 12 and/or the inner skirt 16 by, for example, heat bonding, adhesive, and/or suturing. As shown in the illustrated embodiment, the projections 66 along the outflow edge of the outer skirt 18 can be secured to struts of the frame with sutures 70 while the recesses 68 between adjacent projections can be left unattached to the frame 12 and the inner skirt 16. The outer skirt 18 functions as a sealing member for the prosthetic valve 10 by sealing against the tissue of the native valve annulus, helping to reduce paravalvular leakage past the prosthetic valve 10.

In some embodiments, as shown in FIGS. 1-2, the outer skirt 18 can be configured to extend radially outward from the frame 12 when the prosthetic valve 10 is in a radially expanded configuration. Alternatively, the outer skirt 18 can be configured to form a snug fit with the frame 12 such that it lies against the outer surface of the frame 12 when the prosthetic valve 10 is in the radially expanded configuration. The outer skirt 18 can be formed from any of various synthetic materials or natural tissue (e.g., pericardial tissue). Suitable synthetic materials include any of various biocompatible fabrics (e.g., PET fabric) or non-fabric films, including any of the materials disclosed below for the reinforcing layer 88 of the inner skirt 16. Further details of the outer skirt 18 are also disclosed in U.S. Patent Publication No. 2012/0123529.

As further shown in FIGS. 1-2, the inner skirt 16 in the illustrated embodiment extends from the inlet end 54 of the frame to the fourth row IV of angled struts 28. In other embodiments, the inner skirt 16 can extend from the inlet end 54 of the frame to a location short of the fourth row IV of struts (e.g., to the second row II or the third row III of struts), or the inner skirt can extend the entire height of the frame 12 (e.g., from the inlet end 54 to the outlet end 56). In alternative embodiments, the inner skirt 16 can be positioned and/or sized to extend over a different portion of the frame 12 than the configuration shown in FIGS. 1-2. For example, in some embodiments, the inflow end of the inner skirt 16 can be axially spaced from the inlet end 54 of the frame 12.

Although the inner skirt 16 is typically tubular or cylindrical in shape (forming a complete circle in a cross-sectional profile in a plane perpendicular to the longitudinal axis of the valve), the inner skirt 16 need not extend along the inner surface of the frame 12 in the circumferential direction through 360 degrees. In other words, the inner skirt 16 can have a cross-sectional profile (in a plane perpendicular to the axis of the lumen of the valve) that is not a complete circle. The inner skirt 16 can be initially formed as a flat strip, and then formed to the annular shape by coupling together opposing edge portions, for example, by sewing, thermal bonding, and/or adhesive. Alternatively, the inner skirt 16 can be formed directly in an annular shape, for example, by constructing the inner layer 16 on a cylindrically shaped mandrel as described below.

Figure 5:
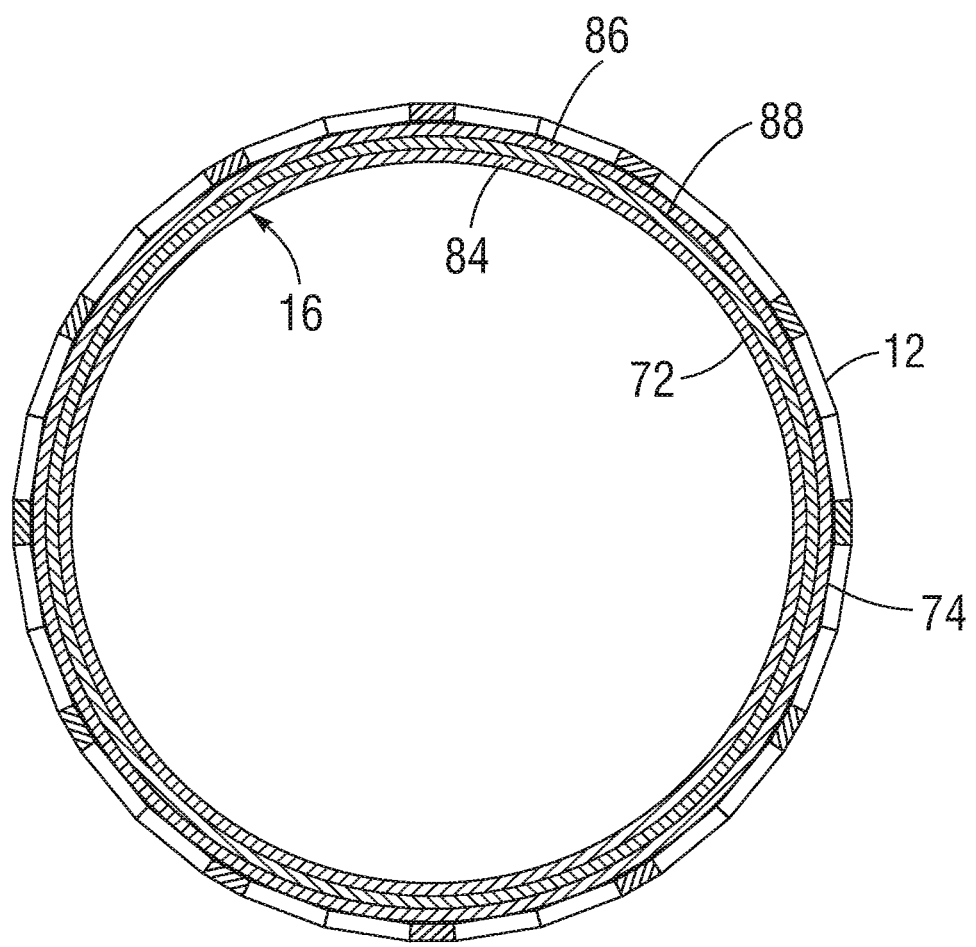
FIG. 5 shows is a cross-sectional view of the prosthetic valve of FIG. 1 taken along line 5-5 of FIG. 1.

Referring to FIG. 5, the inner skirt 16 has a first side 72 defining an inner surface of the inner skirt and a second side 74 defining an outer surface of the inner skirt 16. As described more fully below, the frame-facing side 74 of the inner skirt 16 can have one or more windows or openings, through which an otherwise encapsulated fabric layer is exposed. Sutures can be threaded through the fabric layer of the inner skirt 16 at those windows to secure the inner skirt 16 to the frame 12. The outer skirt 18 is omitted in FIG. 5 for purposes of illustration.

When the inner skirt 16 is mounted to the frame 12, the first side 72 of the inner skirt 16 faces inwardly toward the leaflet structure 14 located interior of the prosthetic valve 10, and the second side 74 of the inner skirt 16 faces outwardly against the inner surface of the frame 12. In particular embodiments, the inner skirt 16 can comprise a reinforcing layer 88 sandwiched between a first covering member 84 and a second covering member 86. In a representative embodiment, the reinforcing layer 88 can be a fabric layer. The first and second covering members 84, 86 can also be referred to as encapsulating layers and form the inner and outer layers, respectively, of the illustrated inner skirt 16. In particular embodiments, the inner surface of the reinforcing layer 88 can be completely covered by the first covering member 84 on the first side 72, and the outer surface of the reinforcing layer 88 is partially covered by the second covering member 86 on the second side 74, with the second covering member 86 defining one or more windows or openings 90 (see FIG. 10) that expose the reinforcing layer 88 on the second side 74.

The reinforcing layer 88 can strengthen the inner skirt 16 to resist tearing. It can also serve as an anchor layer for suturing the inner skirt 16 to the frame 12 and for supporting the cusp edge portions of the leaflets 40, as described more fully below. In addition, the reinforcing layer 88, in cooperation with the encapsulating layers 84, 86, can help decrease (or prevent) paravalvular leakage past the prosthetic valve 10 when in the expanded configuration.

In some embodiments, the reinforcing layer 88 can comprise a woven fabric that is woven from various types of natural or synthetic fibers (or filaments, or yarns, or strands), including but are not limited to: gauze, PET fibers (e.g., Dacron), polyester fibers, polyamide fibers, etc. In certain embodiments, the reinforcing layer 88 can have a knitted or braided structure rather than the woven structure. In certain embodiments, the reinforcing layer 88 can include any of various non-woven fabrics, such as felt. The thickness of the reinforcing layer 88 can vary, but can be less than 6 mil, and desirably less than 4 mil, and even more desirably about 2 mil.

Alternatively, the reinforcing layer 88 can include one or more layers or films formed from any of various semi-crystalline polymeric materials or thermoplastics having aligned or partially aligned (e.g., parallel) molecular chains. Such materials can exhibit anisotropic mechanical properties, such as increased mechanical strength along the longitudinal direction of the molecular chains. Suitable semi-crystalline polymeric materials can include, for example, PTFE, PET, polypropylene, polyamide, polyetheretherketone (PEEK), etc., layers or films of which can be situated between and encapsulated by the encapsulating layers 84, 86, to reinforce the inner skirt 16. Unless otherwise specified, a fabric layer is described in the following description as an exemplary reinforcing layer for illustration purposes, while it is to be understood that a non-fabric layer having sufficiently high tensile strength can also be used as the reinforcing layer.

The encapsulating layers 84, 86 can be made of any suitable biocompatible material. Desirably, the encapsulating layers 84, 86 comprise a material that is relatively less abrasive than the fabric layer to reduce abrasion of the leaflets 40. The encapsulating layers 84, 86 can comprise, for example, a membrane or film formed from non-woven fibers or a non-fibrous material. The biocompatible material used to form the layers 84, 86 may be a non-absorbable polymeric material (i.e., a material that does not dissolve once implanted in the body), and the material may be elastomeric. In addition, any of the encapsulating layers 84, 86 can have a porous microstructure that promotes ingrowth of surrounding tissue to assist in securing the prosthetic valve 10 in a body lumen.

Examples of encapsulating layer materials include, without limitation, ePTFE, unexpanded porous PTFE, polyester or expanded PTFE yarns, PTFE, ultrahigh molecular weight polyethylene (UHMWPE), other polyolefins, composite materials such as ePTFE with PTFE fibers, or UHMWPE film with embedded UHMWPE fibers, polyimides, silicones, polyurethane, hydrogels, fluoroethylpolypropylene (FEP), polypropylfluorinated amines (PFA), other related fluorinated polymers, or various combinations of any of these materials. In particular embodiments, the encapsulating layers 84, 86 can be formed from respective tubes made of a suitable polymeric material (e.g., ePTFE tubes or UHMWPE tubes) that can be bonded to each other when subjected to heat treatment. In some embodiments, the encapsulating layers 84, 86 can be formed from the same type of materials, although different materials can be used to form the encapsulating layers depending on the particular application.

Microporous ePTFE tubes can be made by a number of well-known methods. Expanded PTFE is frequently produced by admixing particulate dry polytetrafluoroethylene resin with a liquid lubricant to form a viscous slurry. The mixture can be poured into a mold, typically a cylindrical mold, and compressed to form a cylindrical billet. The billet can then be ram extruded through an extrusion die into either tubular or sheet structures, termed extrudates in the art. The extrudates comprise an extruded PTFE-lubricant mixture called "wet PTFE." Wet PTFE has a microstructure of coalesced, coherent PTFE resin particles in a highly crystalline state. Following extrusion, the wet PTFE can be heated to a temperature below the flash point of the lubricant to volatilize a major fraction of the lubricant from the PTFE extrudate. The resulting PTFE extrudate without a major fraction of lubricant is known in the art as dried PTFE. The dried PTFE can then be either uniaxially, biaxially, or radially expanded using appropriate mechanical apparatus known in the art. Expansion is typically carried out at an elevated temperature, e.g., above room temperature but below 327° C., the crystalline melt point of PTFE. Uniaxial, biaxial, or radial expansion of the dried PTFE causes the coalesced, coherent PTFE resin to form fibrils emanating from nodes (regions of coalesced PTFE), with the fibrils oriented parallel to the axis of expansion. Once expanded, the dried PTFE is referred to as expanded PTFE ("ePTFE") or microporous PTFE.

UHMWPE is made up of very long chains of polyethylene, with molecular weight numbering in the millions, usually between 2 and 6 million. It is highly resistant to corrosive chemicals, has extremely low moisture absorption and a very low coefficient of friction. It is self-lubricating and highly resistant to abrasion. UHMWPE is processed using compression molding, ram extrusion, gel spinning, and sintering. UHMWPE is available commercially as a powder, in sheets or rods, and as fibers.

The encapsulating layers 84, 86 can be formed by a number of means. For example, in one example, the encapsulating layers 84, 86 can be formed using an electrospinning process, which uses electric force to draw charged threads of polymer solutions or polymer melts up to fiber diameters in the order of some hundred nanometers. In another example, the encapsulating layers 84, 86 can be formed using the centrifugal spinning technique. In centrifugal spinning, the spinning fluid is placed in a rotating spinning head. When the rotating speed reaches a critical value, the centrifugal force overcomes the surface tension of the spinning fluid to eject a liquid jet from the nozzle tip of the spinning head. The jet then undergoes a stretching process and is eventually deposited on the collector, forming solidified nanofibers. Yet in a further example, the encapsulating layers 84, 86 can be formed using an atmospheric plasma spray (APS) technique, which is a special variation of the thermal spray process. APS uses an electric arc to ionize flowing process gases, the hot gas stream can be controlled to melt a very wide range of powder feedstock materials to apply high-quality coatings to a target object. In other embodiments, the encapsulating layers 84, 86 can be formed using any other suitable method including, such as dip coating, spray coating, or melt-spinning. For example, any one of the encapsulating layers 84, 86 can be formed by dipping the fabric layer 88 in a liquefied polymeric material, and then allowing the liquefied polymeric material to cure.

FIGS. 6-10 show one exemplary process of forming the inner skirt 16. Although the use of electrospinning is described below, it is exemplary in nature and is not intended as a limitation. It is to be understood that other processes for depositing a polymeric layer, such as centrifugal spinning, APS, dip coating, and others as described above, can also be used.

Figure 6:
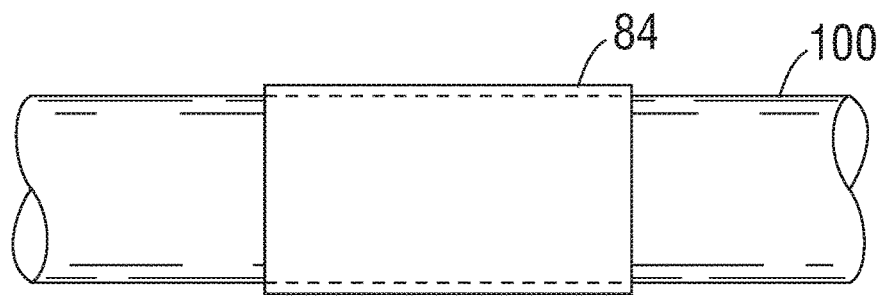
FIG. 6 shows the formation of a first covering member on a mandrel according to an exemplary process of making the inner skirt of the prosthetic valve of FIG. 1.

First, as depicted in FIG. 6, a first covering member 84 comprising a first coating material can be deposited circumferentially around the outer surface of a cylindrically shaped mandrel 100 by means of electrospinning (or using other techniques). As known in the art, the electrospinning system can include a spinneret that is used to extrude a polymer solution or polymer melt to form fibers. To deposit the first covering member 84 over the mandrel 100, the electrospinning system can be configured to rotate the fiber-extruding spinneret in a circular motion around the mandrel 100. Alternatively, the fiber-extruding spinneret can be configured to be stationary while the mandrel 100 is placed in front of the spinneret and rotates about its longitudinal axis.

Figure 7:
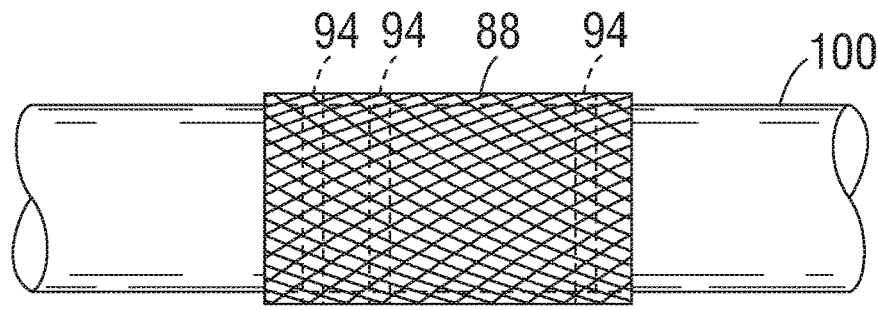
FIG. 7 shows the placement of a fabric layer over the first covering member shown in FIG. 6 according to the exemplary process of making the inner skirt.

Second, as depicted in FIG. 7, the fabric layer 88 can be placed over the first covering member 84. The fabric layer 88 can be in the form of a sheet of fabric material that is tightly wrapped around the first covering member 84. For example, as described above, the fabric layer 88 can have a woven structure that includes threads of warp and weft fibers extending perpendicular to each other. In alternative embodiments, the fabric layer 88 may also be deposited over the first covering member 84. For example, as described above, the fabric layer 88 can include a non-woven fabric, which itself can be formed by means of electrospinning and which desirably has a relatively higher tensile strength than the layers 84, 86. In another example, layer 88 can be a pre-formed braided material that is wrapped around the first covering member 84. In yet another example, layer 88 can be formed by braiding one or more yarns or filaments around the first covering member 84 to form a braided layer around the first covering member.

Figure 8:
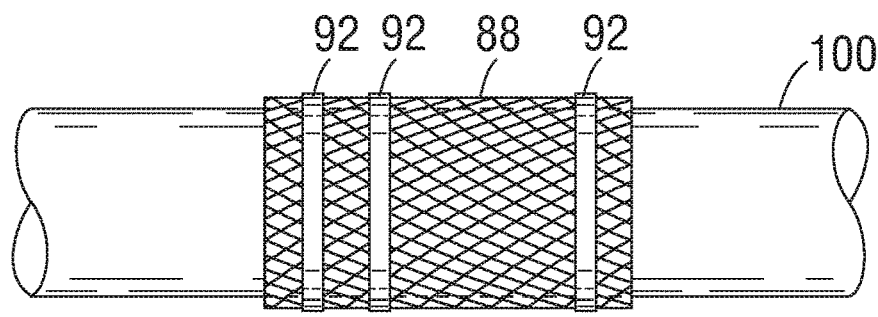
FIG. 8 shows the placement of a plurality of masks over the fabric layer shown in FIG. 7 according to the exemplary process of making the inner skirt.
Figure 9:
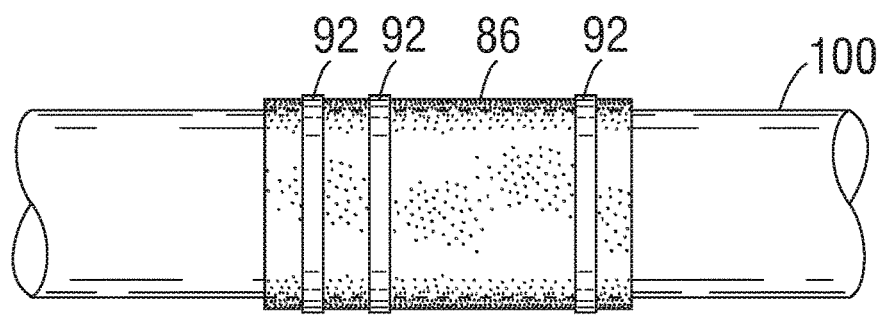
FIG. 9 shows the formation of a second covering member over the fabric layer having masks shown in FIG. 8 according to the exemplary process of making the inner skirt.
Figure 10:
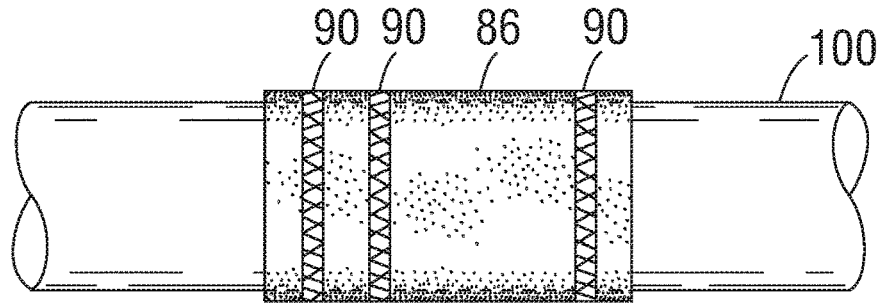
FIG. 10 shows the removal of the masks after forming the second covering member shown in FIG. 9 according to the exemplary process of making the inner skirt.

Third, as depicted in FIG. 8, one or more masks 92 can be placed over the fabric layer 88 at selected areas 94 of the fabric. Fourth, as depicted in FIG. 9, a second covering member 86 comprising of a second coating material can be deposited over the masked fabric layer 88 by means of electrospinning (or using other techniques). Next, as depicted in FIG. 10, the masks 92 are removed after the deposition of the second covering member 86. Accordingly, one or more windows 90 corresponding to the selected areas 94 are created such that the windows 90 expose the underlying fabric layer 88.

In the embodiment shown FIGS. 8-9, the masks 92 can temporarily cover selected areas 94 of the fabric layer 88, and prevent those selected areas 94 from being deposited by the second coating material of the second covering member 86. Alternatively, the selected areas 94 may be functionally masked without the need of applying the physical masks 94. For example, the relevant movement and operation (e.g., activation and/or deactivation) of the fiber-extruding spinneret with respect to the mandrel 100 may be programmed so that the second coating material of the second covering member 86 can only be deposited on portions of the fabric layer 88 that are outside the selected areas 94.

In the embodiment depicted in FIGS. 8-9, three annular bands of masks 92 are shown, respectively corresponding to three selected areas 94 along the outer circumference of the fabric layer 88. As a result, three annular windows 90 are created after the removal of the masks 92, as depicted in FIG. 10. In other embodiments, any one of the masks 92 can have a non-annular shape, so that the corresponding selected area 94 and the resulting window 90 do not completely encircle the fabric layer 88. For example, any one of the masks 92 may have a customized shape at a customized location so as to create a customized window 90. In addition, although three windows 90 are shown in the illustrated embodiment, the inner skirt can be formed with a fewer or greater number of windows and the windows can be positioned at any locations along the skirt. For example, in some embodiments, the inner skirt can be formed with one or more circumferentially extending rows of windows, with each row comprising of a plurality of circumferentially spaced-apart windows. In other embodiments, one or more windows can be formed along the inlet and/or the outlet edge of the inner skirt.

Although not shown, it is to be understood that in each of the steps described above, an anchoring mechanism can be provided to temporarily secure the position of the each layer. As a non-limiting example, layers of PTFE tape can be wrapped around one or both ends of the second covering member 86 to help secure the position of the second covering member 86 to the underlying layers of the assembly and to the mandrel 100 during subsequent processing.

In a representative embodiment, the fabric layer 88 has a plurality of openings that allow the first covering member 84 and the second covering member 86 to fuse together through those openings. In one example, the openings in a fabric layer 88 may be created by weaving, braiding, or knitting fibers or yarns to form the fabric layer. In another example, the fabric layer 88 may have a non-woven, porous structure with openings. In another example, such as when a non-woven fabric (e.g., a felt) is used to form the fabric layer, openings in the fabric layer 88 can be formed by cutting (e.g., laser cutting) openings in the fabric layer.

In one exemplary embodiment, fusion between the first and second covering members 84, 86 through openings in the fabric layer 88 can occur simultaneously during the process of depositing the second covering member 86 over the masked fabric layer 88. As the second coating material extruded from the spinneret is deposited on the fabric layer 88 to form the second covering member 86, some of the second coating material may penetrate through those openings in the fabric layer 88, and fuse with the fibers in the first covering member 84.

In other embodiments, fusion between the first and second covering members 84, 86 may occur after the deposition of the second covering member 86 over the masked fabric layer 88. For example, the assembly shown in FIG. 10 can undergo an encapsulation process whereby the assembly is subjected to heat and/or pressure to cause the first and second covering members 84, 86 to bond to each other through the openings in the fabric layer 88. In addition, the fabric layer 88 may have an axial length that is shorter than the first and second covering members 84, 86 to facilitate bonding of the first and second covering members 84, 86 at their respective ends to encapsulate the fabric layer 88 therebetween. A similar encapsulation process is described in U.S. Patent Publication Nos. 2014/0209238 and 2016/0317305, which are both incorporated herein by reference.

In an exemplary embodiment, ePTFE can be used as the first coating material for depositing the first covering member 84 and/or the second coating material for depositing the second covering member 86. Alternatively, other materials such as UHMWPE, polyurethane composite materials, or any other non-absorbable polymeric materials described above can be used. The inner skirt 16 desirably can have a laminate structure in which the fabric layer 88 is sandwiched between the two fused layers: the first covering member 84 and and second covering member 86. In some embodiments, the same material can be used for depositing the first and second covering members 84, 86. Due to the inter-layer fusion or bonding, the first and second covering members 84, 86 can be merged together, effectively creating a unitary structure (i.e., there is no physical inter-layer boundary), in which the fabric layer 88 is encapsulated. The density of the first covering member 84 can be the same as or different from the density of the second covering member 86. In other embodiments, the first coating material used for depositing the first covering member 84 can be different from the second coating material used for depositing the second covering member 86.

After the first and second covering members 84, 86 are firmly fused together to encapsulate the fabric layer 88, the inner skirt 16 can be removed from the mandrel 100. One or both end portions of the inner skirt 16 can be trimmed to achieve the desired height of the inner skirt. The inner skirt 16 can then be mounted to the frame 12.

Although FIGS. 6-10 and the description above illustrate the process of forming an annularly shaped inner skirt 16, it is to be understood that the same process can be used to form the outer skirt 18. Further, as described above, the inner skirt 16 may be initially formed as a flat strip, and then formed to the annular shape by coupling together its two opposing edges. To form a flat strip, the first and second covering members 84, 86 as well as the fabric layer 88 may be constructed on a flat substrate, instead of the cylindrically shaped mandrel 100 as described above.

Although the process described above uses masking to create the windows 90 on the second covering member 86 of the inner skirt 16, it is to be understood that other methods can be used to create those windows 90. For example, the second covering member 86 can be initially deposited over the entire surface of the fabric layer 88. Then selected areas 94 on the second covering member 86 can be located and removed, for example, by means of laser cutting, chemical erosion, or other means. As a result, windows 90 can be created at the selected areas 94 on the second covering member 86, exposing the underlying fabric layer 88 therein. In another example, the second covering member 86 can be pre-fabricated so that it is devoid of the second coating material in the selected areas 94. Then the pre-fabricated second covering member 86 can be wrapped around the fabric layer 88. As a result, the fabric layer 88 can be exposed through windows 90 created at the selected areas 94. Then, the assembly (the first covering member 84, the fabric layer 88, and the second covering member 86) can undergo the heat- and/or pressure-based encapsulation process as described above, causing the first and second covering members 84, 86 to bond to each other.

The inner skirt 16 can be sutured to the frame 12 at the locations of the windows 90. For example, the inner skirt 16 can be placed on the inside of frame 12. The positions of the windows 90 can be arranged so as to generally correspond to the first, third, and fourth rows of struts 22, 26 and 28, respectively, although other configurations can be used. The inner skirt 16 can also be secured to the struts of the first, third, and fourth rows of struts with sutures extending around the struts and through the fabric layer 88 at the locations of the windows 90, as further described below in connection with FIGS. 11-13. Since the windows in the illustrated embodiment extend continuously around the entire circumference of the inner skirt, a continuous, circumferentially extending whip stitch can be formed along each row of struts and the fabric layer 88 at each window 90.

As described above, the windows 90 can be created at selected locations and can have any of various shapes, allowing the inner skirt to be sutured to the frame at different locations. For example, as noted above, the inner skirt can be formed with rows of circumferentially spaced-part windows, which can allow placement of individual sutures or stitching that does not extend continuously along an entire row of struts, such as at selected portions on the inner skirt that are more prone to tension or stress.

Figure 13:
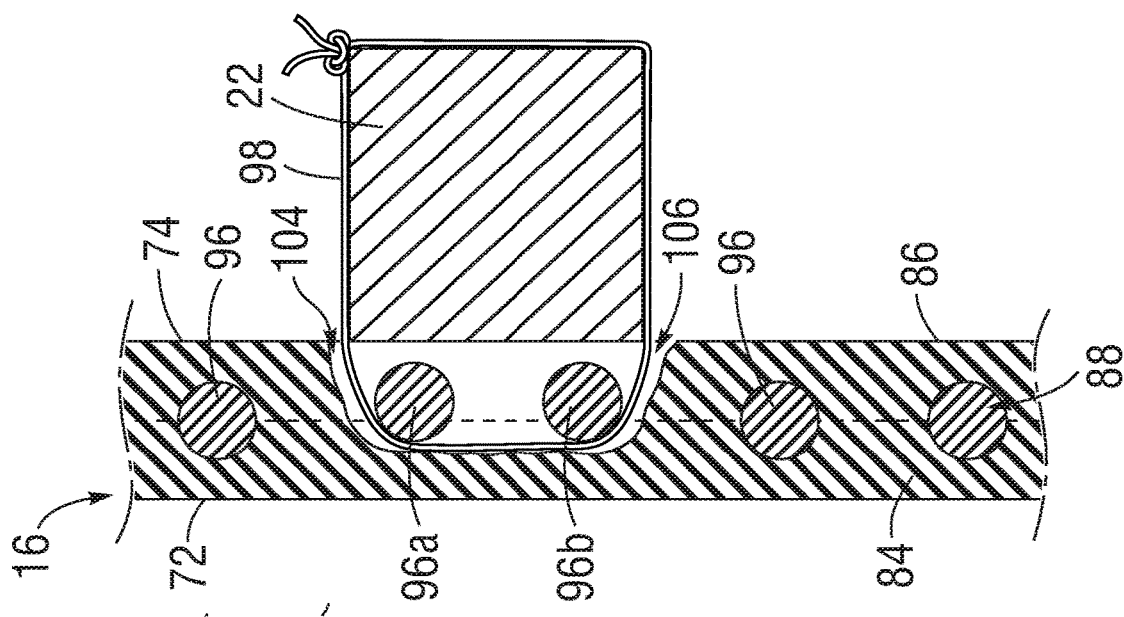
FIG. 13 shows suturing the inner skirt shown in FIG. 11 to an adjacent strut of a prosthetic valve's frame.
Figure 12:
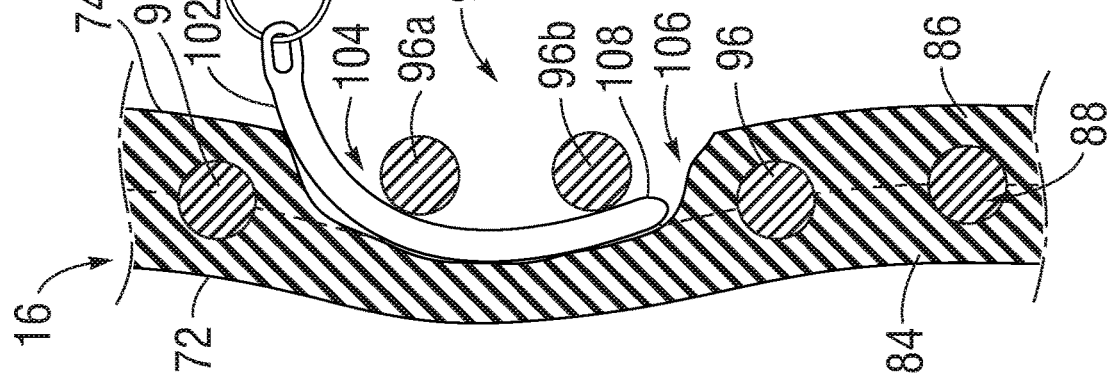
FIG. 12 shows threading a suture through the woven fabric at the window shown in FIG. 11.
Figure 11:
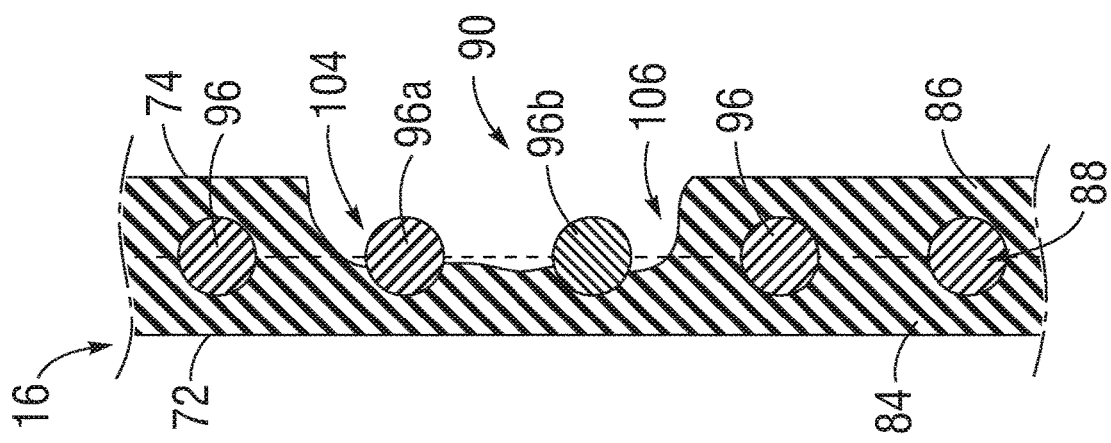
FIG. 11 shows a cross-sectional view of a portion of an inner skirt having a window on one side of the inner skirt exposing the underlying woven fabric.

FIGS. 11-13 illustrate an exemplary method of suturing the inner skirt 16 to the frame 12. FIG. 11 shows a cross-sectional view of a portion of an inner skirt 16 having a first side 72 and a second side 74. As described above, the inner skirt 16 has an encapsulated fabric layer 88 sandwiched between the first covering member 84 on the first side 72 and the second covering member 86 on the second side 74. FIG. 11 also depicts a window 90 on the second covering member 86 of the inner skirt 16, exposing the underlying fabric layer 88. The inter-layer boundary (as indicated by the dashed line) may be absent when the same material is used to form the encapsulating layers 84, 86, which can be fused or bonded together to form a single, unitary structure encapsulating the fabric. In the depicted embodiment, the fabric layer 88 is shown to have a woven structure comprising woven filaments, fibers, or yarns 96. The woven filaments 96 desirably have sufficient strength to serve as anchors to retain sutures 98, as described below.

FIG. 12 schematically shows how to thread a suture 98 between the fabric layer 88 and the first covering member 84 through the window 90. In the depicted embodiment, the suture 98 is attached to a needle 102. The tip 108 of the needle 102 is desirably blunted. By sliding the needle 102 from the second side 74 and through the window 90 while applying light force at the needle tip 108, the first covering member 84 can be slightly pushed away from the fabric layer 88, thus creating a space for the needle 102 to be inserted between the first covering member 84 and the fabric layer 88. As shown, the needle 102 and the attached suture 98 can slide into the fabric layer 88 from a first end 104 of the window 90, pass behind one or more filaments 96 that are exposed by the window 90 (e.g., 96a and 96b), and then slide out of fabric layer 88 at a second end 106 of the window 80. In this manner, the suture 98 does not extend through the entire thickness of the inner skirt 16. In some embodiments, the first covering member 84 may not separate from the fabric layer 88 by insertion of the needle 102 (as depicted in FIG. 12), in which case the needle 102 and the attached suture 98 may be threaded partially through the thickness of the first covering member 84 but does not extend through the entire thickness of the inner skirt.

FIG. 13 schematically illustrates suturing the fabric layer 88 of the inner skirt 16 to an adjacent strut 22 of the frame 12. Desirably, the first side 72 of the inner skirt 16 faces inwardly toward the leaflet structure 14 located interior of the prosthetic valve 10, and the second side 74 of the inner skirt 16 faces outwardly against the frame 12. By threading the needle 102 and the attached suture 98 between the fabric layer 88 and the first covering member 84 through the window 90, the woven filaments 96 between the first and second ends 104, 106 of the window 80 (e.g., 96a and 96b) can collectively serve as anchors to hold the suture 98. The suture 98 can then be wrapped around the adjacent strut 22, thus securing those woven filaments (e.g., 96a and 96b) to the adjacent strut 22. Accordingly, the inner skirt 16 can be securely attached to the frame 12. FIG. 13 depicts a strut 22 for purposes of illustration. It should be understood that the inner skirt 16 can be sutured to other struts of the frame (e.g., 26, 28, 32) in a similar manner.

As described above, the fabric layer 88 may also have a non-woven structure that has no distinct woven threads 96. In such case, the suture 98 may be attached to a needle that has a pointed tip. The needle can be used to pierce the fabric layer 88 and thread the suture 98 through the fabric layer. In this manner, the portion of the fabric layer 88 that is between the first and second ends 104, 106 of the window 90 can function as an anchor to hold the suture 98, which in turns secures that portion of the fabric to the adjacent strut 22. Accordingly, the inner skirt 16 can be securely attached to the frame 12.

Because the suture 98 is routed between the first covering member 84 and the fabric layer 88, it is not exposed on the first side 72 of the inner skirt 16. In other words, the suture 98 is covered by the first covering member 84. The inner surface of the fabric layer is also covered by the first covering member. Therefore, abrasion of leaflets 40 due to repetitive contact between the leaflets 40 and inner skirt 16 and between the leaflets 40 and the sutures 98 during working cycles of the prosthetic valve 10 can be avoided. Desirably, the inner skirt 16 is sutured to the frame 12 only at the one or more windows 90 on the second covering member 86, so that contact between the moveable portions of the leaflets 40 and the sutures 98 can be avoided. Additionally, the first covering member 84 desirably covers the entire extent of the inner surface of the fabric layer, or at least the portions of the fabric layer that would otherwise contact the moveable portions of the leaflet during working cycles of the prosthetic valve. In some embodiments, sutures 98 may pass through the entire thickness of the inner skirt, such as at locations on the inner skirt that would not come in contact with moveable portions of the leaflets.

As noted above, the leaflets 40 can be secured to one another at their adjacent sides to form commissures 58. Each commissure 58 can be secured to a corresponding commissure window 20 of the frame 12, as described in U.S. Patent Publication No. 2012/0123529. The inflow or cusp edges 52 of the leaflets 40 can be sutured to the inner skirt 16 along a suture line that tracks the curvature of the scalloped inflow edge of the leaflet structure. The fabric layer 88 can provide the strength required to retain the sutures. Any suitable suture, such as an Ethibond suture, can be used to secure the leaflets 40 to the fabric layer 88 of the inner skirt.

In some embodiments, the inflow edges 52 of the leaflets 40 are secured to the inner skirt 16 prior to mounting the inner skirt 16 to the frame. After securing the leaflets 40 to the inner skirt 16, the inner skirt is then secured to the frame as described above and the commissures 58 of the leaflets are mounted to the frame. In other embodiments, the inner skirt 16 can be mounted to the frame without the leaflets, after which the inflow edges 52 of the leaflets are then secured to the inner skirt.

In certain embodiments, the inflow edges 52 of the leaflets 40 can be secured to the inner skirt via a thin PET reinforcing strip (not shown), as disclosed in U.S. Pat. No. 7,993,394, which is incorporated herein by reference. As described in U.S. Pat. No. 7,993,394, the reinforcing strip can be sutured to the inflow edges of the leaflets. The reinforcing strip and the lower edges of the leaflets can then be sutured to the inner skirt 16. The reinforcing strip desirably is secured to the inner surfaces of the leaflets 40 such that the inflow edges 52 of the leaflets become sandwiched between the reinforcing strip and the inner skirt when the leaflets and the reinforcing strip are secured to the inner skirt. The reinforcing strip enables a secure suturing and protects the pericardial tissue of the leaflet structure from tears.

As described above, the outer skirt 18 can be constructed in a similar manner as the inner skirt 16. That is, the outer skirt 18 can also have a reinforcing layer (e.g., a fabric layer 88) sandwiched between encapsulating layers 84, 86. Similarly, windows 90 can be created on one of the encapsulating layers 84, 86. Because the outer skirt 18 is attached to the outside of the frame 12, the outer layer 18 is desirably arranged so that the frame 12 faces the side of the outer skirt 18 that has the windows 90. In such arrangement, the outer skirt 18 can be attached to the frame 12 by suturing the encapsulated fabric layer 88 to the frame 12 through the frame-facing windows 90.

Yet in another embodiment, the outer skirt 18 can have the fabric layer 88 being coated with only one of the encapsulating layers 84, 86. While attaching the outer skirt 18 to the frame 12, the outer skirt 18 can be arranged so that the uncoated side of the fabric layer 88 faces inwardly toward the frame 12, so that the outer skirt 18 can be attached to the frame 12 by suturing the exposed fabric layer 88 to the frame 12.

Alternatively, the outer skirt 18 can comprise only the fabric layer 88 without any of the encapsulating layers 84, 86. As such, the outer skirt 18 can be directly sutured to the frame 12. Because the sutures on the outer skirt 18 are not subject to repetitive contact by the moving leaflets 40, abrasion of the leaflets due to the sutures on the outer skirt 18 may be less a concern than the sutures on the inner skirt 16. By eliminating one or both encapsulating layers 84, 86, the outer layer 18 may be constructed thinner, thus reducing the overall profile of the valve 10 when it is crimped to a radially compressed state.

General Considerations

It should be understood that the disclosed embodiments can be adapted to deliver and implant prosthetic devices in any of the native annuluses of the heart (e.g., the pulmonary, mitral, and tricuspid annuluses), and can be used with any of various delivery approaches (e.g., retrograde, antegrade, transseptal, transventricular, transatrial, etc.).

For purposes of this description, certain aspects, advantages, and novel features of the embodiments of this disclosure are described herein. The disclosed methods, apparatus, and systems should not be construed as being limiting in any way. Instead, the present disclosure is directed toward all novel and nonobvious features and aspects of the various disclosed embodiments, alone and in various combinations and sub-combinations with one another. The methods, apparatus, and systems are not limited to any specific aspect or feature or combination thereof, nor do the disclosed embodiments require that any one or more specific advantages be present or problems be solved. The technologies from any example can be combined with the technologies described in any one or more of the other examples. In view of the many possible embodiments to which the principles of the disclosed technology may be applied, it should be recognized that the illustrated embodiments are only preferred examples and should not be taken as limiting the scope of the disclosed technology.

Although the operations of some of the disclosed embodiments are described in a particular, sequential order for convenient presentation, it should be understood that this manner of description encompasses rearrangement, unless a particular ordering is required by specific language set forth below. For example, operations described sequentially may in some cases be rearranged or performed concurrently. Moreover, for the sake of simplicity, the attached figures may not show the various ways in which the disclosed methods can be used in conjunction with other methods. Additionally, the description sometimes uses terms like "provide" or "achieve" to describe the disclosed methods. These terms are high-level abstractions of the actual operations that are performed. The actual operations that correspond to these terms may vary depending on the particular implementation and are readily discernible by one of ordinary skill in the art.

As used in this application and in the claims, the singular forms "a," "an," and "the" include the plural forms unless the context clearly dictates otherwise. Additionally, the term "includes" means "comprises." Further, the terms "coupled" and "connected" generally mean electrically, electromagnetically, and/or physically (e.g., mechanically or chemically) coupled or linked and does not exclude the presence of intermediate elements between the coupled or associated items absent specific contrary language.

Directions and other relative references (e.g., inner, outer, upper, lower, etc.) may be used to facilitate discussion of the drawings and principles herein, but are not intended to be limiting. For example, certain terms may be used such as "inside," "outside,", "top," "down," "interior," "exterior," and the like. Such terms are used, where applicable, to provide some clarity of description when dealing with relative relationships, particularly with respect to the illustrated embodiments. Such terms are not, however, intended to imply absolute relationships, positions, and/or orientations. For example, with respect to an object, an "upper" part can become a "lower" part simply by turning the object over. Nevertheless, it is still the same part and the object remains the same. As used herein, "and/or" means "and" or "or", as well as "and" and "or".

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope of these claims.

We claim:

1. A method for making an implantable prosthetic valve, comprising:
    forming a laminate comprising a fabric layer disposed between first and second covering members, wherein the second covering member includes one or more windows where the fabric layer is exposed;
    placing the laminate against an annular frame;
    suturing the laminate to the annular frame by threading a suture through the fabric layer at the one or more windows of the second covering member and around a portion of the frame; and
    attaching one or more leaflets to the laminate inside of the annular frame, the leaflets being configured to regulate flow of blood through the prosthetic valve.

2. The method of claim 1, wherein the laminate comprises an annular skirt sized and shaped to cover openings in the frame to prevent blood from flowing through the frame openings.

3. The method of claim 2, wherein the skirt is positioned inside of the annular frame.

4. The method of claim 1, wherein the first and second covering members are fused to each other through openings in the fabric layer.

5. The method of claim 1, wherein the act of forming the laminate comprises forming the first covering member by electrospinning, placing the fabric layer on the electrospun first covering member, and forming the second covering member on the fabric layer by electrospinning.

6. The method of claim 5, wherein the act of forming the laminate further comprises masking one or more areas on the fabric layer prior to forming the second covering member so as to form the one or more windows in the second covering member when the second covering member is formed over the fabric layer.

7. The method of claim 1, wherein the act of forming the laminate comprises masking one or more areas on at least one side of the fabric layer with a masking material, dipping the fabric layer in a liquefied polymeric material, allowing the liquefied polymeric material to cure, and removing the masking material to form the one or more windows in the laminate.

8. The method of claim 2, wherein the one or more windows in the second covering member extend continuously around the laminate in a circumferential direction.

9. The method of claim 1, wherein the first and second covering members comprise elastomeric material.

10. The method of claim 9, wherein the elastomeric material comprises ePTFE or UHMWPE or polyurethane.

11. The method of claim 1, wherein the one or more leaflets are attached to the laminate before suturing the laminate to the annular frame.

12. The method of claim 1, wherein the one or more leaflets are attached to the laminate after suturing the laminate to the annular frame.

13. The method of claim 1, wherein each leaflet has a generally U-shaped inlet edge such that the inlet edges of the one or more leaflets form an undulating, scalloped curvature, and wherein the one or more leaflets are sutured to laminate along a suture line that tracks scalloped curvature of the inlet edges.

14. The method of claim 1, wherein the suture is attached to a needle and suturing the laminate to the annular frame comprises inserting the needle into the fabric layer in a first direction at a first end of a window, passing the needle behind one or more filaments of the fabric layer, and removing the needle from the fabric layer in a second direction at a second end of the window.

15. The method of claim 14, wherein the needle and the attached suture extend through a space between fabric layer and the first covering member.

16. The method of claim 1, wherein the suture does not extend through an entire thickness of the laminate.

17. A method for making an implantable prosthetic valve, comprising:
attaching one or more leaflets to an inner skirt; and
attaching the inner skirt to an annular frame;
wherein the leaflets are configured to permit the flow of blood from an inflow end to an outflow end of the frame and block the flow of blood from the outflow end to the inflow end of the frame;
wherein the inner skirt comprises a fabric layer disposed between first and second covering members, the second covering member comprising at least one window exposing a portion of the fabric layer;
wherein the inner skirt is attached to the annular frame via a suture extending through the portion of the fabric layer exposed by the window.

18. The method of claim 17, wherein the suture is routed between the first covering member and the fabric layer.

19. The method of claim 17, wherein the at least one window comprises one or more annular windows, through which the inner skirt is sutured to the annular frame.

20. The method of claim 19, wherein the annular windows comprise a first window located adjacent the inlet end of the frame, a second window located adjacent the outlet end of the frame, and a third window located between the first and second windows.

* * * * *